(12) United States Patent  
Mueller et al.

(10) Patent No.: US 10,885,645 B2  
(45) Date of Patent: Jan. 5, 2021

(54) DETERMINATION OF A WAVINESS INDEX OF HAIR

(71) Applicant: Henkel AG & Co. KGaA, Duesseldorf (DE)

(72) Inventors: Burkhard Mueller, Duesseldorf (DE); Torsten Lechner, Langenfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 39 days.

(21) Appl. No.: 16/470,919

(22) PCT Filed: Dec. 11, 2017

(86) PCT No.: PCT/EP2017/082235  
§ 371 (c)(1),  
(2) Date: Jun. 18, 2019

(87) PCT Pub. No.: WO2018/114434  
PCT Pub. Date: Jun. 28, 2018

(65) Prior Publication Data  
US 2020/0090353 A1 Mar. 19, 2020

(30) Foreign Application Priority Data

Dec. 20, 2016 (DE) .......................... 10 2016 225 678

(51) Int. Cl.  
*G06K 9/00* (2006.01)  
*G06T 7/40* (2017.01)  
(Continued)

(52) U.S. Cl.  
CPC .............. *G06T 7/40* (2013.01); *A45D 44/005* (2013.01); *G06K 9/2036* (2013.01);  
(Continued)

(58) Field of Classification Search  
CPC ............ G06T 7/40; G06T 2207/30196; G06T 2207/10024; G06K 9/2026; G06K 9/3233;  
(Continued)

(56) References Cited

U.S. PATENT DOCUMENTS 6,333,985 B1 * 12/2001 Ueda .................... A45D 44/005  
382/100  
6,723,308 B2 * 4/2004 Browning .............. A61K 8/362  
424/401

(Continued)

FOREIGN PATENT DOCUMENTS

DE     102014220077 A1    4/2016  
JP       H04105045 A     4/1992

OTHER PUBLICATIONS

EPO, International Search Report and Written Opinion issued in International Application No. PCT/EP2017/082235, dated Mar. 8, 2018.

(Continued)

*Primary Examiner* — Amir Alavi  
(74) *Attorney, Agent, or Firm* — Lorenz & Kopf, LLP

(57) ABSTRACT

In various exemplary embodiments a method for determining the waviness index of hair is provided. The method may comprise the steps of determining and/or establishing at least one hair examination region in at least one digital image, in which hair is depicted, determining a plurality of different brightness values in the hair examination region, and determining the waviness index of hair on the basis of the plurality of brightness values.

19 Claims, 6 Drawing Sheets

(51) Int. Cl.
*A45D 44/00* (2006.01)
*G06K 9/20* (2006.01)
*G06K 9/32* (2006.01)

(52) U.S. Cl.
CPC ...... *G06K 9/3233* (2013.01); *A45D 2044/007* (2013.01); *G06T 2207/10024* (2013.01); *G06T 2207/30196* (2013.01)

(58) Field of Classification Search
CPC ............ A45D 2044/007; A45D 44/005; A45D 44/00; G01N 21/57; G01N 33/4833; G01N 2201/0221; G06Q 30/0633; G06Q 30/0631
See application file for complete search history.

(56) References Cited

U.S. PATENT DOCUMENTS

| | | | |
|---|---|---|---|
| 7,226,585 B2 * | 6/2007 | Browning | A61K 8/362 424/401 |
| 8,428,382 B2 * | 4/2013 | Sato | A45D 44/005 382/254 |
| 8,484,155 B2 * | 7/2013 | Yamaguchi | A61B 5/448 706/54 |
| 10,231,531 B2 * | 3/2019 | Witchell | G01N 21/31 |
| 10,379,032 B2 * | 8/2019 | Godfrey | G06T 7/90 |
| 2007/0100555 A1 | 5/2007 | Ladjevardi | |
| 2014/0313302 A1 | 10/2014 | Franke et al. | |
| 2017/0206678 A1 | 7/2017 | Kowalczyk et al. | |
| 2020/0090353 A1 * | 3/2020 | Mueller | G06K 9/3233 |
| 2020/0249161 A1 * | 8/2020 | Mueller | G06Q 30/0631 |

OTHER PUBLICATIONS

Svanera et al: "Figaro, hair detection and segmentation in the wild", 2016 IEEE, International Conference on Image Processing (ICIP), Sep. 25, 2016, pp. 933-937, retrieved on Aug. 3, 2016.

Lefaudeux et al.: "New luster formula for the characterization of hair tresses using polarization imaging", Journal of Cosmetic Science, Mar./Apr. 2009, No. 60, pp. 153-169, United States, retrieved from the Internet: http://www.ncbi.nlm.nih.gov/pubmed/19450417.

* cited by examiner

DETERMINATION OF A WAVINESS INDEX OF HAIR

CROSS-REFERENCE TO RELATED APPLICATION

This application is a U.S. National-Stage entry under 35 U.S.C. § 371 based on International Application No. PCT/EP2017/082235, filed Dec. 11, 2017, which was published under PCT Article 21(2) and which claims priority to German Application No. 10 2016 225 678.5, filed Dec. 20, 2016, which are all hereby incorporated in their entirety by reference.

TECHNICAL FIELD

The present disclosure relates to a method and a device for determining a waviness index of hair, and a method for determining an individual hair treatment recommendation.

BACKGROUND

Shiny, healthy-looking hair can constitute an important cosmetic objective, which can be achieved by employing cosmetic products for enhancing shine.

The suitability of a shine-enhancing product for a hair type can be dependent on the shape of the hair, for example whether the hair is straight or wavy.

Users are often unaware of which shine-enhancing products are best suited for their hair type (or their hair shape) in order to provide shiny hair. One reason for this may be that they are currently unable to objectively assess their hair shape. Until now, the waviness of hair was assessed either subjectively, i.e. by visual inspection, or for example indirectly by the use of surrogate methods. For example, a combability of the hair can be determined as a surrogate method of this kind and can make it possible to ascertain the straightness/waviness of the hair indirectly.

A determination of this kind (for example quantification) of the combability can be performed relatively complexly in a laboratory, but is not suitable for an end user, and also cannot be used by employing a mobile application.

A further reason why users are often unaware of which shine-enhancing products are suitable for them may be that the products are not provided with information indicating for which hair shape they are suitable.

There is thus a need for a quantitative assessment of the waviness of hair, for example of a hairstyle. Simple practicability without any, or with only low equipment outlay would also be desirable here, such that the waviness of the hair can be ascertained also by a user, for example.

There is also a need for a product recommendation for a shine-enhancing product which is suitable for a hair shape of a user.

BRIEF SUMMARY

Methods of determining the waviness index of hair, devices for determining the waviness index of hair, and methods for determining an individual hair treatment recommendation are provided herein. In an embodiment, a method for determining the waviness index of hair includes determining and/or establishing at least one hair examination region in a digital image in which hair is depicted, determining a plurality of different brightness values in the hair examination region of the digital image, and determining the waviness index of hair on the basis of the plurality of brightness values.

BRIEF DESCRIPTION OF THE DRAWINGS

The present disclosure will hereinafter be described in conjunction with the following drawings, wherein like numerals denote like elements, and.

DETAILED DESCRIPTION

Figure 1A:
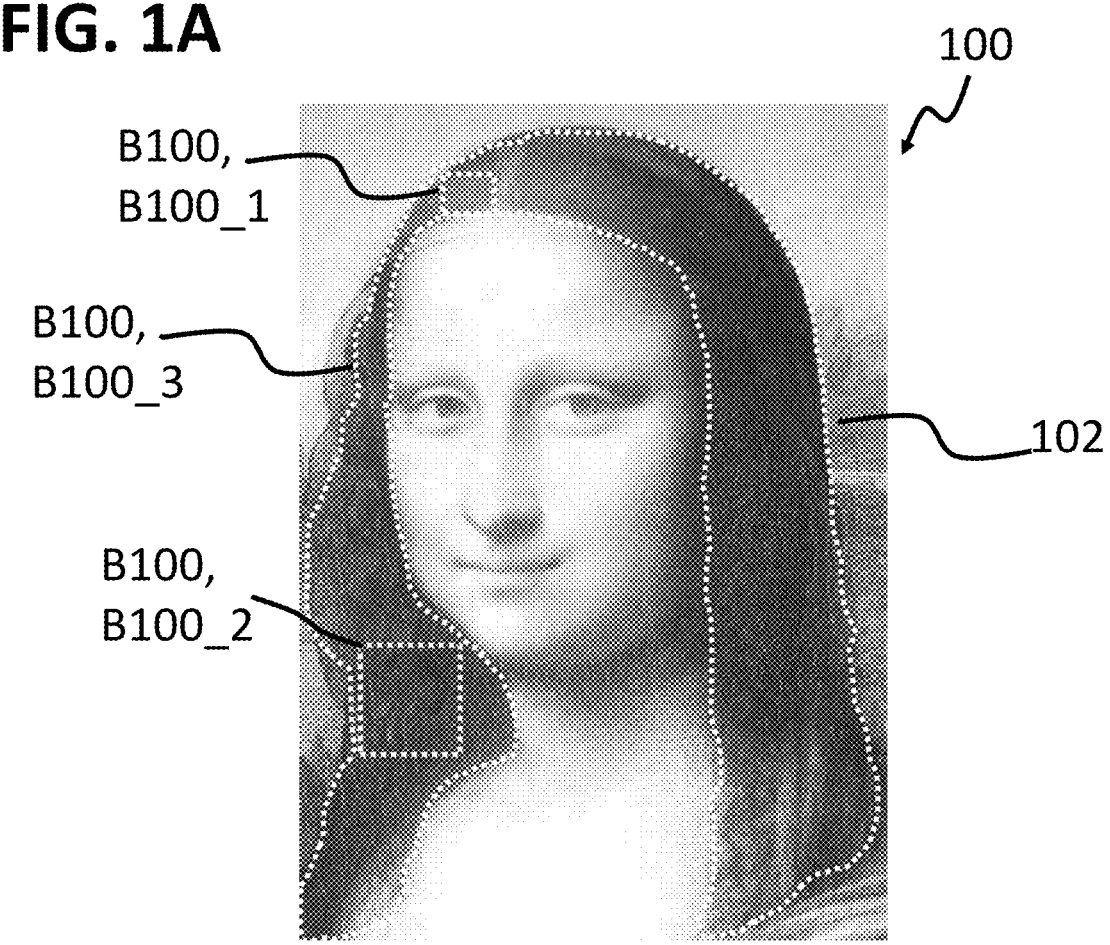
FIG. 1A is an image showing hair for use in a method for determining a waviness index of hair according to various exemplary embodiments and optionally in a method for determining an individual hair treatment recommendation in accordance with various exemplary embodiments.

The following detailed description is merely exemplary in nature and is not intended to limit the disclosure or the application and uses of the subject matter as described herein. Furthermore, there is no intention to be bound by any theory presented in the preceding background or the following detailed description.

A method for determining a degree of waviness of hair, which for example can be quantified as waviness index, is provided in various exemplary embodiments.

The determined waviness index can be used in various exemplary embodiments to determine a shine-enhancing product recommended for hair having the determined waviness index.

In various exemplary embodiments the determination of the waviness index can be used to determine the success of a change in shape of the hair, for example the success of a straightening or curling process.

In various exemplary embodiments the fact that a (for example digital) image of wavy hair has stronger light/dark contrasts than an image of straight hair can be utilised to determine the waviness of hair.

A digital image in which hair is depicted can be recorded in various exemplary embodiments by employing a digital camera.

In various exemplary embodiments the hair can be illuminated by diffuse light whilst the image is being recorded. Strong reflections, which could be produced by an intense directed light source and which could hinder a differentiation between hair samples of different waviness indexes on the basis of the brightness difference can thus be avoided or mitigated.

In various exemplary embodiments the method can be performed with only little or no equipment outlay. For example, the method can be performed by employing an app on a tablet or a smartphone. For example, this can allow a user to determine the waviness index of their hair, for example their hairstyle, even without professional assistance and without having to provide a hair sample for examination, for example using a smartphone or tablet for recording a digital image of the hairstyle and with the straightness index being determined by employing the smartphone/table, wherein the smartphone/tablet can be used in various exemplary embodiments to provide the image to an external data processing device, for example a cloud, and to receive the results determined there and to display them to the user.

In various exemplary embodiments a user can obtain an exact product recommendation tailored to their hair waviness, for example for enhancing hair shine, without having to perform a separate hair assessment, but for example easily, by recording or being able to record one or more images of their hair using their smartphone and being able to evaluate this by employing an app for determining a hair treatment, in particular a haircare product.

In various exemplary embodiments a method for determining the waviness index of hair is provided. The method may comprise the steps of determining and/or establishing at least one hair examination region in at least one digital image, in which hair is depicted, determining a plurality of different brightness values in the hair examination region, and determining the waviness index of hair on the basis of the plurality of brightness values.

In various exemplary embodiments the step of determining a plurality of brightness values can comprise determining a minimal brightness value and a maximum brightness value, wherein the step of determining the waviness index of hair on the basis of the plurality of brightness values can comprise determining a quotient of the maximum brightness value and the minimum brightness value.

In various exemplary embodiments the step of determining a plurality of brightness values can comprise determining a brightness distribution, wherein the step of determining the waviness index of hair on the basis of the plurality of brightness values can comprise determining the breadth of the brightness distribution.

In various exemplary embodiments the method may also comprise a step of recording the at least one digital image.

In various exemplary embodiments the method can also comprise a step of illuminating the recorded hair with diffuse light during the recording of the at least one digital image.

In various exemplary embodiments the step of recording the at least one digital image may comprise arranging a camera for recording the digital image in such a way that an angle between a main direction, from which the diffuse light illuminates the hair, and an optical axis of the camera has an angle of at least about 75°.

In various exemplary embodiments the step of recording the at least one digital image may comprise recording a plurality of digital images, wherein hair from a different area of a hairstyle can be shown in each image of the plurality of digital images.

In various exemplary embodiments the step of determining the waviness index of hair can comprise determining a common hairstyle waviness index on the basis of the plurality of brightness values from the plurality of digital images.

In various exemplary embodiments the step of establishing the at least one hair examination region may comprise establishing the position and/or shape and/or size of the hair examination region.

In various exemplary embodiments the step of determining and/or establishing at least one hair examination region may comprise determining a hair display region in which the hair is depicted in the digital image, and establishing at least part of the hair display region as the at least one hair examination region.

In various exemplary embodiments the at least one hair examination region may comprise the entire hair display region.

In various exemplary embodiments the digital image may be parameterised in a colour space which has a brightness as one parameter.

In various exemplary embodiments the method may also comprise a step of displaying the determined results.

In various exemplary embodiments a device for determining the waviness index of hair is provided. The device may comprise a data processing device and a display device, and the device may be designed to carry out the method for determining the waviness index of hair in accordance with various exemplary embodiments.

In various exemplary embodiments a method for determining an individual hair treatment recommendation is provided. The method may comprise a step of determining a waviness index of hair in accordance with various exemplary embodiments and a step of determining a hair treatment, in particular a haircare product, on the basis of the determined waviness index value.

In various exemplary embodiments the hair treatment may comprise a hair treatment for enhancing shine. In various exemplary embodiments the haircare product may comprise a haircare product for enhancing shine.

In various exemplary embodiments the waviness index may have a value from a multi-staged waviness scale, which can be associated with wavinesses ranging from very minor to very strong, wherein the hair treatment, in particular the haircare product, for enhancing shine may be one from a plurality of hair treatments, in particular haircare products, for enhancing shine, wherein each of the plurality of hair treatments, in particular haircare products, for enhancing shine can be associated with a shine-enhancing stage, and wherein the determination of a hair treatment, in particular a haircare product, on the basis of the determined waviness index, can comprise a determination of a hair treatment, in particular a haircare product, with a higher shine creation stage for hair having a higher waviness index.

Exemplary embodiments of the present disclosure are shown in the figures and will be explained in greater detail hereinafter.

Reference is made in the following detailed description to the accompanying drawings, which form part of the present application and in which specific embodiments in which the present disclosure can be carried out are shown by way of illustration. In this regard, directional terms such as "above", "below", "ahead", "behind", "front", "rear", etc. are used in relation to the orientation of the described figure(s). Since components of embodiments can be positioned in a number of different orientations, the directional terms are used by way of illustration and are in no way limiting. It goes without saying that other embodiments can be used and structural or logical changes can be made without departing from the scope of protection of the present disclosure. It goes without saying that the various exemplary embodiments described herein can be combined with one another unless specifically stated otherwise. The following detailed description therefore is not to be interpreted as limiting, and the scope of protection of the present disclosure is defined by the accompanying claims.

A digital image can be understood herein to mean a data packet which can be displayed by a data processing system as a two-dimensional (planar) arrangement of image dots (also referred to as pixels), for example in a coordinate system which has an x-axis and a y-axis, wherein each image dot comprises at least one image position as x,y-coordinate pair and intensity information, wherein the intensity information for example can be displayed as the colour of a pixel of a monitor or a printed dot of a printed image. The intensity information can relate in a colour image to individual colour channels. The digital image can be for example a photo recorded using a digital camera or an individual image of a video sequence recorded using a digital camera.

FIG. 1A shows an image 100 of a user 102 in which the hair of the user 102 is depicted, for use in a method for determining a waviness index of hair according to various exemplary embodiments and optionally in a method for determining an individual hair treatment recommendation in accordance with various exemplary embodiments;

In order to be able to determine the waviness of hair in accordance with various exemplary embodiments, the image 100 can be provided digitally. The digital image 100 can be provided for example to a data processing device.

In various exemplary embodiments the digital image 100 can be an image 100, for example what is known as a black and white image, which comprises merely brightness information, for example a greyscale image, in which white can be assigned the greatest brightness and black can be assigned the lowest brightness.

In various exemplary embodiments the digital image 100 can be a colour image 100 which is coded in a colour space (for example L*a*b*) with a plurality of parameters, wherein one of the parameters can be a brightness. In order to carry out the method described herein, for example for determining the waviness index, examination of the image can be limited to the brightness parameter.

In various exemplary embodiments an image U100 can be provided, which is not digitalised. The image U100 can be converted into the digital image 100 for example by being scanned.

In various exemplary embodiments an image U100 can be provided which is parameterised in a colour space having no brightness parameter, for example RGB. The image U100, for example by transformation, can be converted into a colour space having a brightness parameter, for example L*a*b*. For a subsequent examination for determining the waviness of hair, merely the brightness parameter can then be used, and the further parameters (for example hue, saturation) can be ignored.

In various exemplary embodiments at least one hair examination region B100 can be determined in the image 100. Here, three hair examination regions B100_1, B100_2, B100_3 are shown. The hair examination regions B100_1 and B100_2 are additionally shown on an enlarged scale in FIGS. 1B and 1C.

Figure 1B:
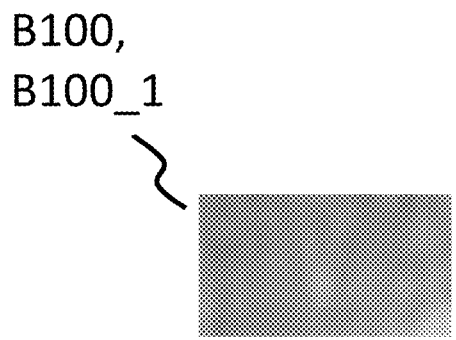
FIGS. 1B and 1C shown enlarged hair examination regions of the image from FIG. 1.
Figure 1C:
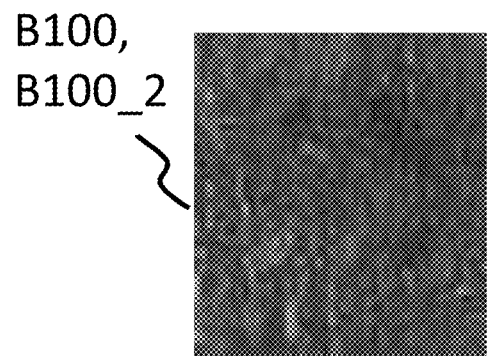

In order to quantify the difference, immediately evident to the viewer, in the waviness of the hair in the hair examination regions B100_1 from FIG. 1B (relatively straight) and B100_2 from FIG. 1C (relatively wavy), an image processing method can be applied to the digital image 100 in various exemplary embodiments, by which method for example each of the hair examination regions B100_1, B100_2 can be examined separately.

Figure 2A:
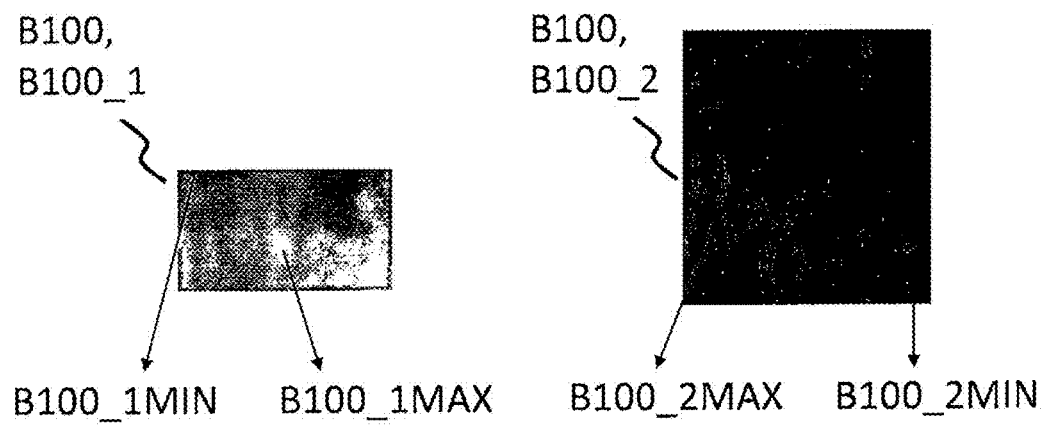
FIG. 2A shows the enlarged hair examination regions from FIG. 1B together with a marking of a maximum and a minimum brightness value in accordance with various exemplary embodiments.

FIG. 2A shows the enlarged hair examination regions B100_1, B100_2 from FIG. 1B with a marking in each case of a maximum brightness value MAX (here B100_1MAX for the hair examination region B100_1 and B100_2MAX for the hair examination region B100_2) and a minimum brightness value MIN (here B100_1MIN for the hair examination region B100_1 and B100_2MIN for the hair examination region B100_2) in accordance with various exemplary embodiments.

Figure 2B:
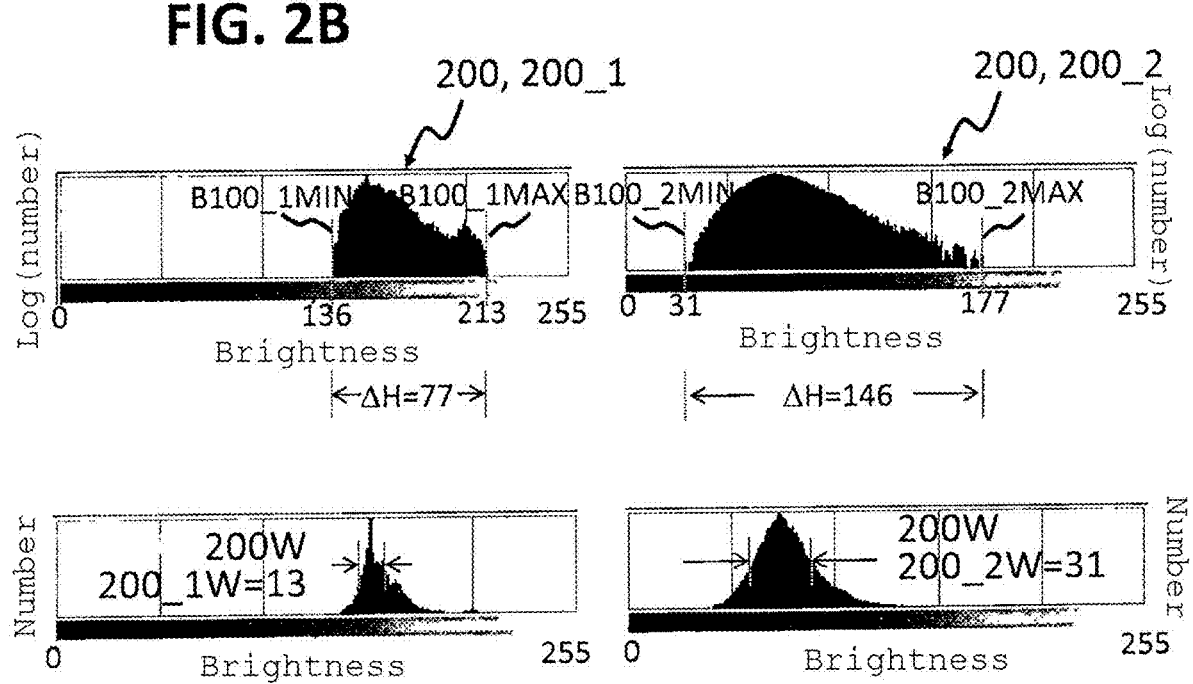
FIG. 2B shows brightness distributions from FIG. 1B together with a marking of a maximum and a minimum brightness value in accordance with various exemplary embodiments.

FIG. 2B shows brightness distributions 200_1, 200_2 of the hair examination regions B100_1 and B100_2 respectively from FIGS. 1A, 1B, 1C and 2A in accordance with various exemplary embodiments. Here the upper graph in each case shows the brightness distribution with logarithmic vertical axis display, and the lower graph in each case shows the brightness distribution with linear vertical axis display.

In various exemplary embodiments the region of the image 100 in which hair (for example main hair, i.e. for example without eyebrows, beard, etc.) is shown can be referred to as the hair display region. The hair display region may comprise a plurality of image dots of the digital image 100, which depict the hair 102 and which can form a continuous area or an area existing of a plurality of individual areas. A plane in which the hair region can be arranged can be determined for example by the x-axis and the y-axis of the digital image.

In various exemplary embodiments the digital image 100 may also comprise, in addition to the hair display region, further display regions in which for example objects, body parts, etc. may be displayed. The hair examination region B100 may be selected in various exemplary embodiments such that no part of the other display regions falls in the hair examination region B100.

In various exemplary embodiments the hair examination region B100 may comprise a partial region of the hair examination region. The exemplary hair examination regions B100_1, B100_2 shown in FIG. 1A to FIG. 2B each comprise a partial region of the hair display region.

In various exemplary embodiments the hair examination region B100 may comprise the entire hair examination region B100. The exemplary hair examination region B100_3 shown in FIG. 1A comprises the entire hair display region.

In various exemplary embodiments, for example if only hair is shown in the digital image 100, the hair examination region B100 can comprises substantially the entire region of the digital image 100. In this case the hair examination region B100 can be rectangular, for example square.

In various exemplary embodiments the hair examination region B100 may have any shape, for example the hair examination region B100, apart from being rectangular (for example square), may also be triangular, polygonal with a number of sides other than three or four, elliptical, round or shaped in any other way.

In various exemplary embodiments in which the hair examination region B100 comprises the entire hair display region, the hair examination region B100 may consequently have a one-part or multi-part area which can be examined for a subsequent analysis, for example for a determination of brightness values, even in the case of the multi-part area as a single hair examination region B100.

In various exemplary embodiments the at least one hair examination region B100 may comprise a plurality of hair examination regions B100; see for example in FIG. 1A the hair examination regions B100_1, B100_2 and B100_3. In various exemplary embodiments, in a subsequent analysis, for example when determining a plurality of different brightness values, each hair examination region B100_1, B100_2 and B100_3 of the plurality of hair examination regions B100_1, B100_2 and B100_3 can be examined separately, i.e. the plurality of different brightness values can be determined separately for each of the plurality of hair examination regions B100_1, B100_2 and B100_3.

In various exemplary embodiments the step of determining and/or establishing the at least one hair examination region B100 can comprise determining the hair display region in the image 100, for example by employing known methods, and establishing the at least one hair examination region B100.

In other words, in accordance with various exemplary embodiments, the face of a user, i.e. all face areas which do not contain any hair or only little hair, and the background are masked out in a first step.

For example, the defining of the at least one hair examination region B100 may mean that, as described above, the entire hair display region is defined as the hair examination region B100, and/or one or more hair examination region(s) B100 can be defined, for example in an automated manner, by employing the data processing device, for example with inclusion of predetermined conditions. For example the size and/or number of hair examination regions B100 can be predefined, for example by action of a user, and the hair examination regions B100 can then be defined in an automated manner, for example by employing a suitable software, for example such that between the hair examination regions B100 a minimum and/or maximum distance remains, such that the hair display region is covered as uniformly as possible, and the like.

In various exemplary embodiments a software can be used for the above-described determinations. Here, any software that provides the above-described functionality can be used. In various exemplary embodiments, for example in a case in which a smartphone or a tablet is used to carry out the method for determining a waviness index of hair, the software can be provided as an app.

In FIG. 1A the image 100 shows (in addition to the hair examination region B100_3 comprising the entire hair display region) two differently positioned hair examination regions: a first hair examination region B100_1 and a second hair examination region B100_2.

In various exemplary embodiments the two hair examination regions B100_1, B100_2 can be examined separately from one another, for example in such a way that a separate plurality of brightness values is determined for each of the hair examination regions B100_1, B100_2, and on that basis a separate waviness index is determined for each of the hair examination regions B100_1, B100_2.

In various exemplary embodiments the plurality of differently positioned hair examination regions B100_1, B100_2 can be used to obtain a reference point for a distribution of wavy and/or straight hair in a hairstyle. For example, in a hairstyle the hair close to the scalp (in the example the hair examination region B100_1) may be straight, whereas the hair close to the tips (in the example the hair examination region B100_2) may be wavy.

In various exemplary embodiments a difference in the appearance of wavy hair compared to straight hair, which is also shown in an imaging, for example a two-dimensional imaging, can be used to determine the waviness index of hair, which can be a quantification of the waviness of hair.

In the case of wavy hair, partial regions of the hair can be arranged relative to one another, for example with an angular offset relative to one another and/or partially one above the other, in such a way that there is not a continuous area (or at most only small areas) of adjacently arranged hairs provided. As a result, even if the hair is illuminated with diffuse light in the case of wavy hair, there may be a shadowing of hair on hair arranged therebeneath/therebehind, whereas in the case of straight hair such a shadowing cannot occur, or can occur only to a much lesser extent.

Brightness values of the shown hair can thus have a greater heterogeneity in the case of wavy hair than in the case of straight hair.

By examining the brightness values of the shown hair, for example by determining a plurality of brightness values of the hair and evaluating the brightness values, for example by setting them in relation to one another (i.e. forming a quotient), forming a difference, deriving statistical parameters, or the like, a measure for the heterogeneity of the brightness values of the shown hair can be determined in various exemplary embodiments.

In various exemplary embodiments, for example in a comparison with provided reference values and/or in a comparison of brightness values for different hair examination regions B100 with one another, an absolute and/or relative waviness index for the hair can be determined, for example for the hair in the hair examination region B100 and/or for a hairstyle.

In various exemplary embodiments the step of determining a plurality of brightness values may comprise determining a minimum brightness value MIN and a maximum brightness value MAX.

The step of determining the waviness index of hair on the basis of the plurality of brightness values, in various exemplary embodiments, may comprise determining a brightness ratio (a quotient) $HV=MAX/MIN$ between the maximum brightness value MAX and the minimum brightness value MIN.

In FIG. 2B a first brightness distribution 200_1 for the first hair examination region B100_1 and a second brightness distribution 200_2 for the second hair examination region B100_2 are shown by way of example; in the upper part of the drawing scaled logarithmically in the direction of the vertical axis and in the lower part of the drawing scaled linearly in the direction of the vertical axis. Absolute values of the y-axis may be irrelevant and are omitted. For example, y-axis values can be standardised to a maximum value of 1.

The depictions are to be understood merely as an illustration of the method. In various exemplary embodiments, when determining the maximum brightness value MAX and the minimum brightness value MIN, it is possible for example to dispense with a step of determining the brightness distribution, and instead the maximum brightness value MAX and the minimum brightness value MIN can be determined directly, for example by employing a data processing device, for example by employing a smartphone, a tablet, a laptop or other computer, on which for example a software, for example an app, can be installed.

In various exemplary embodiments the brightness ratio can be associated with a waviness index, for example by employing a comparison with reference values. The reference values may have been created beforehand, for example by employing empirical data, and for example may be stored in a manner retrievable as a reference database for the data processing device, for example in a memory of the data processing device.

The reference data can comprise for example a multi-staged waviness scale, for example with at least two waviness indices (for example from "very minor" to "very strong"), for example three to five waviness indices, for example at most 20 waviness indices, which has at least one measurement value for each of the waviness indices of the waviness scale, which measurement values can be determined by employing the determined plurality of different brightness values, for example the brightness ratio.

An exemplary assignment of brightness ratios to waviness indices is provided in the following table:

| Light/dark ratio HV | Hair waviness (waviness index) |
| --- | --- |
| ≤1.3 | very minor |
| >1.3-3.0 | moderate |
| >3.0-10.0 | strong |
| >10.0 | very strong |

In various exemplary embodiments the brightness ratio can also be used to determine a relative waviness index, for example by employing comparison of the brightness ratios for different hair examination regions with one another and/or various hairstyles.

The comparison of the brightness ratios with one another, for example by forming a quotient of the brightness ratios, can make it possible to assess the waviness of the compared hair examination regions B100 or hairstyles relative to one another, for example to determine which of the regions or the hairstyles is wavier. In the case of a quotient greater than 1, the region for which the brightness ratio forms the dividend is the wavier region, and in the case of a quotient less than 1, the region for which the brightness ratio forms the divisor is the wavier region. A comparison of more than two hair examination regions B100 with one another in pairs and/or in each case with a common reference hair examination region can make it possible to determine a waviness sequence on the basis of quotients of various size.

In the example in FIG. 2B the first hair examination region B100_1 (in which the hair appears to be straight) has a minimum brightness value of MIN=136 and a maximum brightness value MAX of 213. This gives a brightness ratio of HV=213/136=1.57.

The second hair examination region B100_2 (in which the hair appears to be wavy) has a minimum brightness value of MIN=31 and a maximum brightness value MAX of 177. This gives a brightness ratio of 177/31=5.71.

The absolute values of the brightness ratios HV show that the hair examination region B100_2 with the brightness ratio of HV=5.71 (compared with HV=1.57 for the hair examination region B100_1) comprises the wavier hair.

Generally, in various exemplary embodiments, brightness ratios in a range of from approximately 1.1 to approximately 100 can be expected, for example of from approximately 1.3 to approximately 20.

On the basis of a ratio of the brightness ratios of 5.71/1.57=3.6, it has also been demonstrated that the wavier hair is depicted in the hair examination region of the dividend (i.e. the hair examination region B100_2).

The step of determining the waviness index of hair on the basis of the plurality of brightness values, in various exemplary embodiments, may comprise determining a brightness difference ΔH=MAX−MIN between the maximum brightness value MAX and the minimum brightness value MIN.

In various exemplary embodiments the measurement values provided in the reference data can be standardised, for example by employing a number of possible brightness values (in the example from FIG. 2B, 256 grey scales). An improved comparability of the reference data with images that may comprise a variety of brightness values, for example more or fewer than 256 possible brightness values, can thus be made possible.

In the example in FIG. 2B the first hair examination region B100_1 (in which the hair appears to be straight) has a minimum brightness value of MIN=136 and a maximum brightness value MAX of 213. This gives a brightness difference of 77 and a standardised brightness difference of 0.3.

The second hair examination region B100_2 (in which the hair appears to be wavy) has a minimum brightness value of MIN=31 and a maximum brightness value MAX of 177. This gives a brightness difference of 146 and a standardised brightness difference of 0.57.

The absolute values of the brightness differences (146 compared to 77 or standardised 0.57 compared to 0.3 respectively) show that the hair examination region B100_2 comprises the wavier hair.

On the basis of a ratio of the brightness differences of 146/77=1.9, it has also been demonstrated that the wavier hair is depicted in the hair examination region of the dividend (i.e. the hair examination region B100_2).

In various exemplary embodiments the step of determining a plurality of brightness values can comprise determining a brightness distribution 200, i.e. determining how many image elements for all possible brightness values have a particular brightness value.

In various exemplary embodiments the step of determining the waviness index of hair on the basis of the plurality of brightness values comprises determining a value 200 W for the breadth of the brightness distribution 200.

In various exemplary embodiments the determined breadth of the brightness distribution 200 may be associated with a waviness index from a plurality of waviness indices.

For the association of the waviness index to breadth, that described above for the brightness difference and an association of a waviness index to brightness difference may apply, mutatis mutandis, for example in respect of a comparison of the determined brightness difference with reference data, and/or in respect of a comparison of determined brightness difference values, for example of different hair examination regions B100.

In various exemplary embodiments the breadth of the brightness distribution may be at least one of a full width at half maximum, a standard deviation, an equivalent width, or any other measure that specifies a breadth of the distribution.

In the example in FIG. 2B the first hair examination region B100_1 (in which the hair appears to be straight) has a breadth of 200_1W=13 and a standardised breadth of 0.05.

The second hair examination region B100_2 (in which the hair appears to be wavy) has a breadth of 200_2W=31 and a standardised breadth of 0.12.

The absolute values of the breadth show that the hair examination region B100_2 comprises the wavier hair.

On the basis of a ratio of the breadths of 31/13=2.4, it has also been demonstrated that the wavier hair is depicted in the hair examination region of the dividend (i.e. the hair examination region B100_2).

In various exemplary embodiments any other measures can be used instead of the aforementioned measures or in addition thereto, provided said other measures are suitable for quantifying the difference in the brightness distributions for straight hair and for wavy hair. For example, in order to make the determination of the brightness difference more robust in respect of outliers, a mean value can be used from the plurality of the lowest values, for example the two, three or four lowest values, or a percentage, for example five to fifteen, for example ten %, of the lowest values of the brightness distribution, and, instead of the maximum value MAX, a mean value can be used from for example the two, three or four highest values, or a percentage, for example five to fifteen, for example ten %, of the highest values of the brightness distribution.

In various exemplary embodiments two or more of the determined values can be combined, for example a breadth and a difference value, for example from a single value, which can then be compared for example with the database values in order to determine the waviness index.

By employing the hair examination regions B100 distributed in the hair display region, it can be made possible for wavy and/or straight regions in the hair display region to be identified, for example in a case in which the hair display region comprises an entire hairstyle.

In various exemplary embodiments a plurality of the hair examination regions B100 can be averaged, for example with the use of known averaging methods.

In various exemplary embodiments a smartphone, a tablet, a laptop or the like may be suitable for carrying out the method for determining the waviness index of hair. In various exemplary embodiments the software does not need to be produced on the smartphone, the tablet, the laptop, etc. For example, it may be sufficient if the smartphone or the like is connected by the Internet to a computer. In such a case the calculations can be performed for example by employing the computer, and the result can be provided to the smartphone/tablet or the like.

Figure 3A:
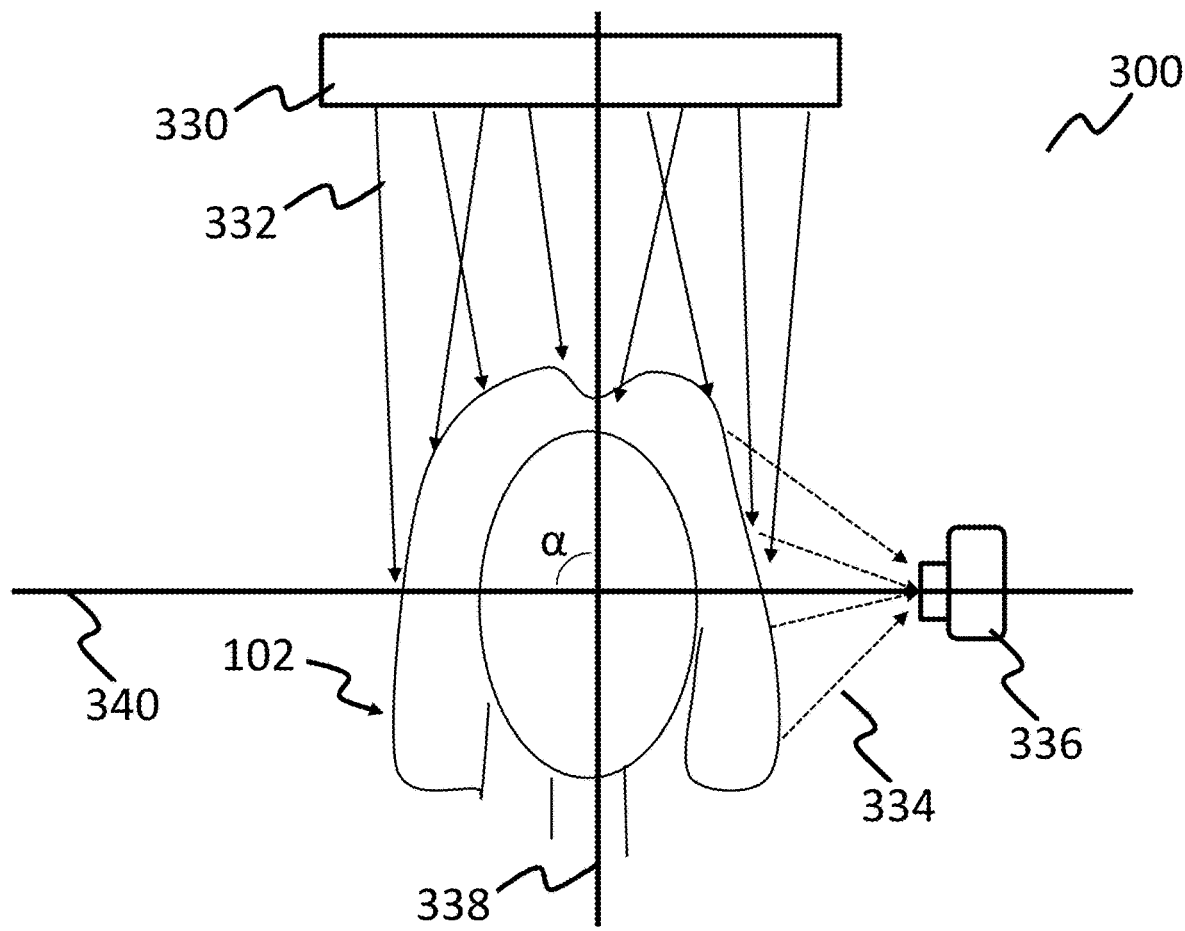
FIGS. 3A and 3B show schematic depictions of an arrangement for carrying out a method for determining a waviness index of hair in accordance with various exemplary embodiments.
Figure 3B:
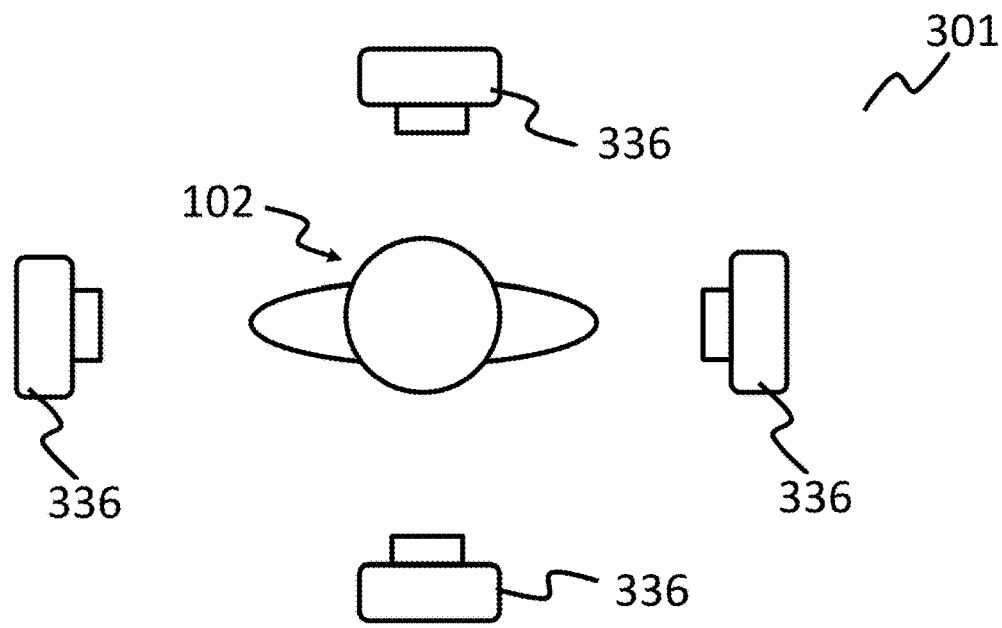

FIGS. 3A and 3B show schematic depictions 300, 301 of an arrangement for carrying out a method for determining a waviness index of hair in accordance with various exemplary embodiments.

In various exemplary embodiments an arrangement for carrying out the method for determining a waviness index of hair in accordance with various exemplary embodiment may comprise a camera 336, for example a digital camera, for example a camera of a device, for example of a smartphone, a tablet, a laptop, or any other digital camera. In various exemplary embodiments an analogue camera can also be used and the recorded images can be digitalised for application of the method for determining the waviness index of hair can be provided for the method. In various exemplary embodiments the camera 336 can comprise a digital video camera, wherein at least one individual image of a video sequence recorded by employing the video camera can be used for the execution of the method for determining a waviness index.

In various exemplary embodiments an arrangement for carrying out the method for determining the waviness index of hair in accordance with various exemplary embodiments may also comprise a light source 330. The light source 330 can be designed and arranged, for example above the head of a user 102, such that hair of the user 102 is illuminated by light 332 irradiated by employing the light source 330 whilst images in which the hair of the user 102 is depicted are recorded. The light source 330 may for example provide an illuminance in a range of from approximately 100 Lux to approximately 100000 Lux, for example of from approximately 200 to approximately 10000 Lux, for example of from approximately 500 Lux to approximately 2000 Lux.

In various exemplary embodiments the light 332 can be diffuse light 332. In the case of an artificial light source 330, this can be achieved for example by employing a diffusor, for example a diffusing plate, or for example by illumination of a room ceiling, a reflection screen, or the like, for example above the user 102, with the light source 330.

In various exemplary embodiments a natural light source 330, for example the sun, can also be used as the light source 330. In various exemplary embodiments a direct irradiation of sun onto the hair of the user can be avoided, for example by arranging the user in partial shade.

In various exemplary embodiments, reflections (for example strong, highlighting reflections) on the hair that would result in a very high brightness value, having approximately the same maximum for hair of any waviness index (which could lead to a misinterpretation of the waviness index, for example of the degree of waviness) can be avoided by employing the diffuse illumination.

In various exemplary embodiments the user 102 can be arranged such that his/her head is upright, i.e. the top side of the head points upwardly, for example in the direction of the light source 330.

In various exemplary embodiments the camera 336 can be arranged during the recording of the image such that at least some of the hair of the user 102 is shown in the image. In various exemplary embodiments the camera 336 can be arranged such that the lens of the camera is arranged at the height of the upper ear parts of the user and the optical axis 340 thereof is substantially perpendicular to the hair surface of the imaged hair. Thus, on the one hand, it is possible to record an image of hair regions of the user 102 that can be depicted in the image primarily for a waviness impression given by a hairstyle of the user 102, and, on the other hand, at least in the case of illumination substantially from above, it can be ensured that an angle $\alpha$ between a main illumination direction 338 and the optical axis 340 of the camera 336 does not fall below a minimum angle and does not exceed a maximum angle. The angle $\alpha$ can lie for example in a range of from approximately 75° to approximately 105°, for example from approximately 85° to approximately 95°. In an arrangement of the camera 336 at a different angle to the main illumination direction 338, for example with the optical axis 340 substantially parallel to the main illumination direction 338, a shadowing (and thus differences in brightness) might also not be discernible in the image in the case of wavy hair, or might be discernible to a lesser extent.

In various exemplary embodiments, as shown in FIG. 2B, recorded images of the hair of the user 102 can be taken from different directions, i.e. from different hair regions.

If only one image is recorded, an image of the hair of the user on the back of the head can be recorded in various exemplary embodiments, because the back of the head typically has the greatest continuous hair surface if an image of the entire head of the user is recorded. However, in various exemplary embodiments a hair region of the user 102 other than the single recorded hair region can also be used.

In various exemplary embodiments, when recording various hair regions, images from the left and/or the right side of the head can also be recorded, and/or images of any hair region considered to be useful for determining the waviness of the hair of the user 102.

In various exemplary embodiments, when recording three or more images, an arrangement of the recorded regions may be symmetrical, for example the images recorded from the side of the head can be arranged symmetrically, i.e. at identical angles, in order to record the back of the head (in FIG. 2B both the right and left side of the head for example are recorded at an angle of 90° in order to record the back of the head).

For the further execution of the method for determining a waviness index of hair, a data processing device can be used, as described above for example and in conjunction with FIG. 6, for example a smartphone, a tablet, or the like.

In various exemplary embodiments those areas in which no hair or little hair is recorded, for example facial areas and/or background regions, can be eliminated from the images, for example in a known manner, for example by application of a morphing filter. In other words the hair display region, which primarily may contain only hair, can be determined and the image region that is not the hair display region can be discarded.

In various exemplary embodiments a brightness value can be determined for each of the remaining image elements, i.e. a hair examination region can comprise the entire hair display region. Alternatively, in various exemplary embodiments at least one partial region of the hair display region can be established as hair examination region, and the determination of the brightness values can be carried out for the partial region of the hair display region.

In various exemplary embodiments a maximum brightness value can be determined for the hair examination region, for example the hair display region, for example by averaging the lightest 10% of the brightness values. Furthermore a minimum brightness value can be determined for the hair examination region, for example the hair display region, for example by averaging the darkest 10% of the brightness values. As described above for example, instead of using the lightest/darkest 10% for determining the maximum/minimum brightness value, other measures for determining a brightness difference of image elements in the image can be used, for example the highest brightness value MAX and the lowest brightness value MIN, a breadth of the brightness distribution, or the like.

In various exemplary embodiments a brightness ratio, i.e. a quotient of the brightness values, can be determined from the maximum brightness value and the minimum brightness value, wherein in principle it may be irrelevant which of the brightness values is used as a dividend and which is used as a divisor. In the present case, in conformity with the above-shown table of brightness ratios (also referred to as the light/dark ratio), the maximum brightness value can be the dividend and the minimum brightness value can be the divisor, and therefore a brightness ratio of >1 can be given.

Accordingly, a waviness index, for example a waviness index from "very minor" to "very strong", can be associated with the determined brightness ratio (the same may apply if other measures are used for determining the brightness differences).

In various exemplary embodiments an individual treatment recommendation, for example a haircare product suitable for the waviness index, can be determined on the basis of a waviness index determined as described above for various exemplary embodiments.

The haircare product can be a product from a group of haircare products for which it is known or is to be expected that their suitability for application to hair may be dependent on the waviness of the hair, i.e. that they may be particularly well suited for hair having a given waviness index.

In various exemplary embodiments the group of haircare products can comprise, for example, haircare products for enhancing hair shine.

An association of waviness indices and suitable haircare products, for example shine-enhancing products, can be provided for example in the form of a predefined database, which for example can be based on empirical data, for example in a memory of the data processing device.

The suitable haircare products in this case can comprise chemical product groups and/or specific product names under which they could be purchased for example by the user.

The haircare products can be associated with the waviness indices in different stages, or conversely the group of haircare products can be divided into a plurality of care stages, for example shine-enhancing stages, and to this end waviness indices for which the haircare products of the corresponding shine-enhancing stage may be suitable can be established.

For shine-enhancing products, ingredients for example, such as dimethicones (average shine creation), apricot kernel oil (high shine creation) and/or phenyltrimethicone (very strong shine creation), can be responsible for different shine-enhancing stages. Straight hair may naturally be shinier than wavy hair. This can be taken into consideration in the product recommendation by recommending products that create a stronger shine for hair that is more strongly waved.

Accordingly, in various exemplary embodiments a user can obtain an exact product recommendation tailored to their hair waviness, for example for enhancing hair shine, without having to perform a separate hair assessment, but for example easily, by recording or being able to record one or more images of their hair using their smartphone and being able to evaluate this by employing an app for determining a haircare product.

In various exemplary embodiments the waviness index may have a value from a multi-staged waviness scale, which can be associated with wavinesses ranging from very straight to very wavy, wherein the haircare product for enhancing shine may be one from a plurality of haircare products for enhancing shine, wherein each of the plurality of haircare products for enhancing shine can be associated with a shine-enhancing stage, and wherein the determination of a haircare product on the basis of the determined waviness index can comprise a determination of a haircare product with a higher shine creation stage for hair having a higher waviness index.

The following table shows an exemplary association of product recommendations for hair waviness indices:

| Hair waviness (waviness index) | Product recommendation |
| --- | --- |
| very minor | Product 1 for minor shine enhancement, containing trisiloxane (1%) |
| moderate | Product 2 for moderate shine enhancement, containing dimethicone (1%) |
| strong | Product 3 for strong shine enhancement, containing apricot kernel oil (1%) |
| very strong | Product 4 for very strong shine enhancement, containing phenyltrimethicone (1%) |

In the table, the names "product 1", etc. can be general names for the product groups, and/or can be representative for one or more product names under which the user could purchase the product in question.

In various exemplary embodiments the haircare product can comprise another haircare product instead of or additionally to a shine-enhancing product, the suitability of which other haircare product may be dependent on the waviness of the hair to be treated, the other haircare product for example being a hair conditioner, a hair fixer/gel/mousse, or the like.

A result of the determination of the individual treatment recommendation, preferably the haircare product for enhancing shine, may be provided to the user, for example displayed or made accessible in another way, for example by voice output.

It may also be preferred that the individual treatment recommendation includes recommending the use/recommending against the use of haircare products that can be identified to the individual on the basis of QR codes, NFC chips, bar codes or RFID chips.

Alternatively, the individual treatment recommendation may include recommending the use of haircare products that have been produced individually for the determined waviness index and of initiating an ordering process, preferably by calling up a website of a manufacturer of individual haircare products.

In various exemplary embodiments the method for determining the waviness index of hair can be performed prior to the application of a method for changing the waviness of hair, for example a smoothing method (for example by employing a conditioner, a hair mask, a perm, a relaxer, a straightener and/or a straightening iron) or a curling/waving method (for example by employing a perm or curlers). For example, it can thus be ascertained whether or at what points a treatment of the hair might be necessary.

Alternatively or additionally, the waviness index can be determined in various exemplary embodiments after the application of the method for changing the waviness. For example, the efficacy of the method for changing the waviness can thus be determined. To this end, the ratio of the waviness index after the treatment and the waviness index prior to the treatment can be determined in various exemplary embodiments.

Figure 4:
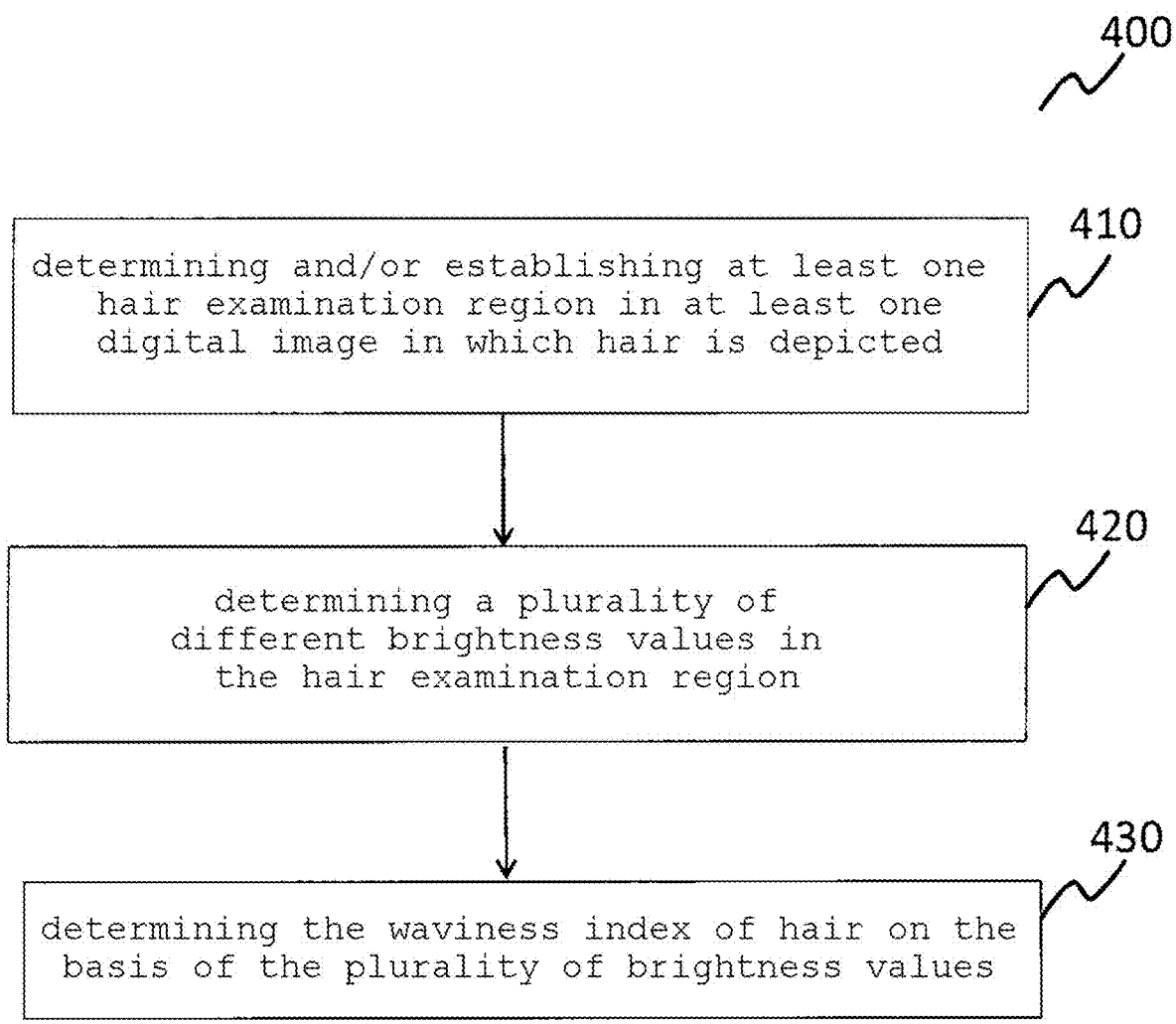
FIG. 4 shows a flow diagram of a method for determining a waviness index of hair in accordance with various exemplary embodiments.

FIG. 4 shows a flow diagram 400 of a method for determining the waviness index of hair in accordance with various exemplary embodiments.

In various exemplary embodiments the method may comprise the steps of determining and/or establishing at least one hair examination region in at least one digital image, in which hair is depicted (in 410), determining a plurality of different brightness values in the hair examination region (in 420), and determining the waviness index of hair on the basis of the plurality of brightness values (in 430).

Figure 5:
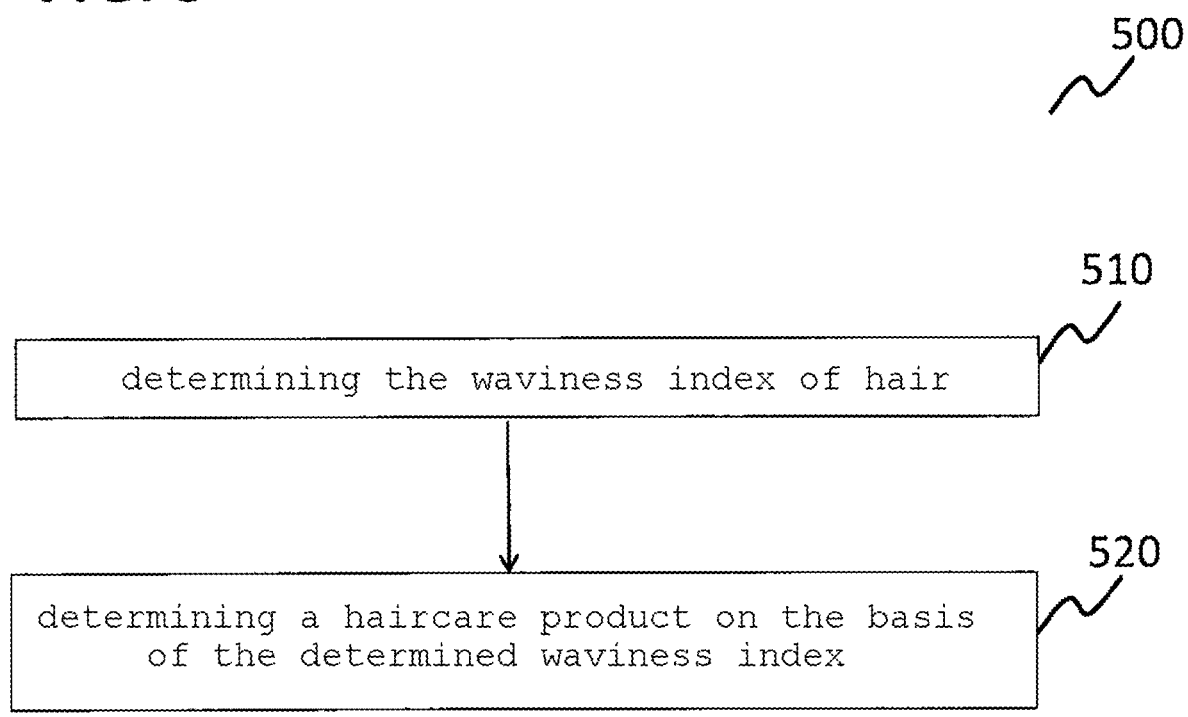
FIG. 5 shows a flow diagram of a method for determining a haircare product in accordance with various exemplary embodiments.

FIG. 5 shows a flow diagram 500 of a method for determining the waviness index of hair in accordance with various exemplary embodiments.

In various exemplary embodiments the method may comprise a step of determining a waviness index of hair (in 510), for example in accordance with different above-described exemplary embodiments, and a step of determining an individual treatment recommendation, preferably a haircare product for enhancing shine, on the basis of the determined waviness index (in 520).

Figure 6:
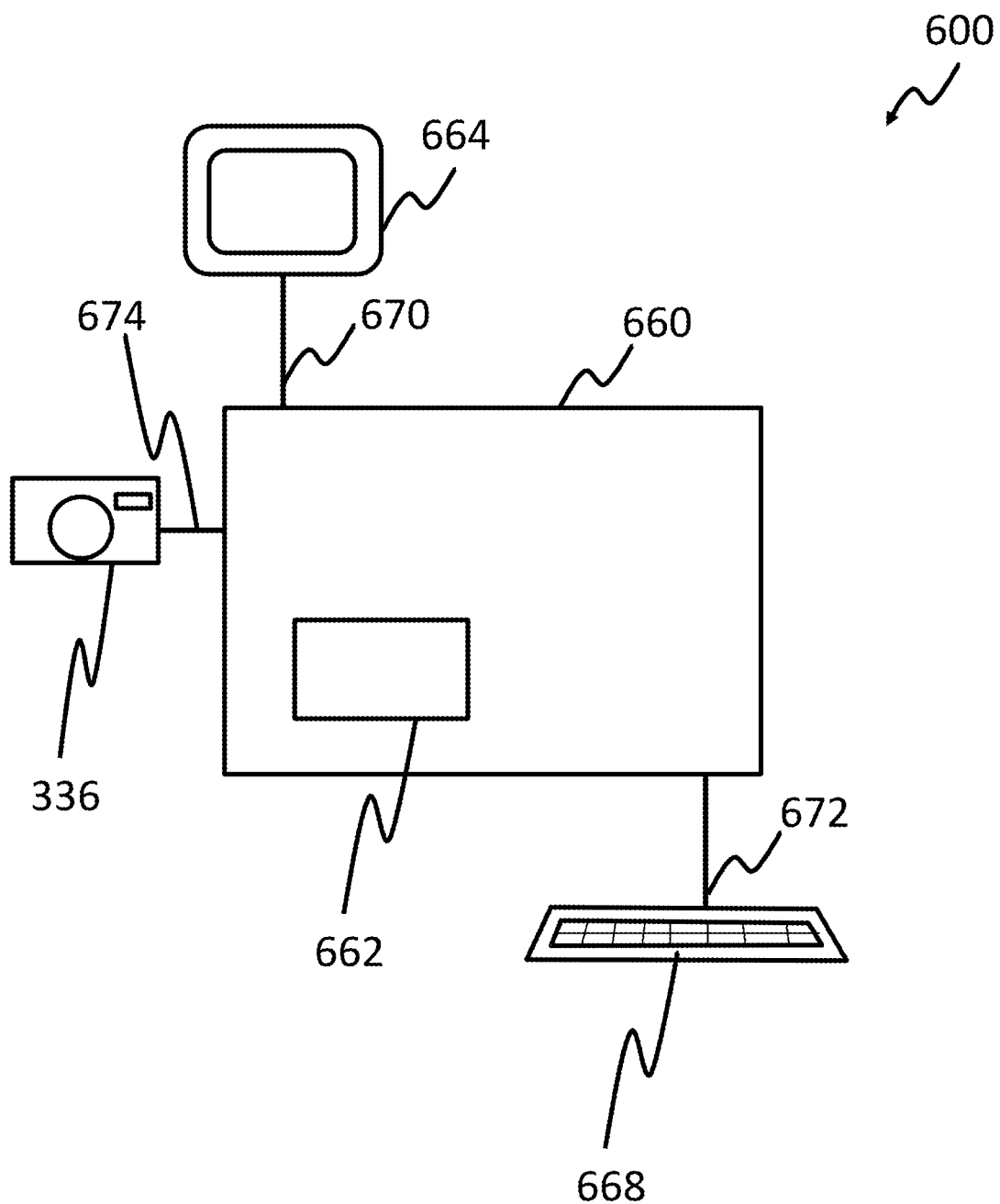
FIG. 6 shows a graphical depiction of a device for determining a waviness index of hair in accordance with various exemplary embodiments.

FIG. 6 shows a graphical depiction of a device 600 for determining the waviness index of hair in accordance with various exemplary embodiments. The device 600 may also be designed to determine an individual treatment recommendation, preferably a haircare product for enhancing shine, in accordance with various exemplary embodiments.

In various exemplary embodiments the device 600 for determining the waviness index of hair and/or for determining an individual treatment recommendation, preferably a haircare product for enhancing shine, can comprise a data processing device 660.

The data processing device 660 can comprise for example a computer, a tablet, a smartphone, a laptop or any other data processing device which is suitable for carrying out the method for determining the waviness index of hair, for determining a haircare product, or the method for determining an individual treatment recommendation in accordance with various exemplary embodiments. By way of simplification, the data processing device 660 herein is also referred to as a computer 660. The data processing device 660 may comprise a processor 662, for example a microprocessor.

In various exemplary embodiments the device 600 for determining the waviness index of hair and/or for determining an individual treatment recommendation, preferably a haircare product for enhancing shine, can comprise a display device 664.

The display device 664 may be for example the screen of a smartphone, of a PC, of a laptop or of another device 600 for determining the waviness index of hair and/or for determining a haircare product. The display device 664 may be used for example to display results of the method for determining the waviness index of hair and/or for displaying an individual treatment recommendation, preferably a haircare product for enhancing shine, for requesting input parameters for carrying out the method, or the like.

The display device 664 may be connected to the data processing device 660 by employing a first data connection 670. The display device 664 may exchange data with the data processing device 660 by employing the first data connection 670. In the case in which the device 600 comprises a smartphone, a tablet or the like, the display device 664 and the first data connection 670 may be integrated in the device 600.

In various exemplary embodiments the device 600 for determining the waviness index of hair and/or for determining a haircare product may comprise a camera 336.

The camera 336 can be designed in accordance with various exemplary embodiments to record a digital image 100 of hair 102, for example hair of a user, for example as described above.

The at least one camera 336 in accordance with various exemplary embodiments may comprise a digital camera or a video camera, i.e. a camera 104 which can be designed to record a plurality of individual images as a time sequence.

In various exemplary embodiments the device 600 for determining the waviness index of hair and/or for determining a haircare product may comprise a second data connection 674 between the computer 660 and the camera 336. Data can be transmitted from the computer 660 to the camera 336 by employing the second data connection 674, for example for (for example conventional) software control of the camera 336. Furthermore, data, for example the digital image(s) recorded by the camera 336, can be transmitted to the computer 660 by employing the second data connection 674. In the case in which the device 600 comprises a smartphone, a tablet or the like, the camera 336 and the second data connection 674 may be integrated in the device 600.

In various exemplary embodiments it is possible in the device 600 for determining the waviness index of hair and/or for determining a haircare product to dispense with a camera 336, for example if the data processing device 660 is provided with the digital image 100 in some other way, for example by employing data transmission.

The data processing device 660 can be designed to process the image, received from the camera 336 or in some other way, by employing an image processing software, for example with use of the processor 662, for example so as to determine the hair display region in the received image in the known manner and so as to determine the waviness index of hair as described above for various exemplary embodiments. The image processing software can comprise an app in various exemplary embodiments.

In various exemplary embodiments the data processing device 600 may comprise an input device 668 for providing information to the data processing device 600, for example a keyboard, a mouse, a touch-sensitive surface of the display device 664, or the like.

The input device 668 may be connected to the data processing device 660 by employing a third data connection 672. The input device 668 may exchange data with the data processing device 660 by employing the third data connection 672. In the case in which the device 600 comprises a smartphone, a tablet or the like, the input device 668 and the third data connection 672 may be integrated in the device 600.

Further advantageous embodiments of the method will become clear from the description of the device, and vice versa.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for determining the waviness index of hair, comprising the steps of:
    determining and/or establishing at least one hair examination region in a digital image in which hair is depicted;
    determining a plurality of different brightness values in the hair examination region of the digital image; and
    determining the waviness index of hair on the basis of the plurality of brightness values.

2. The method according to claim 1,
    wherein the step of determining a plurality of brightness values comprises determining a minimum brightness value and a maximum brightness value; and
    wherein the step of determining the waviness index of hair on the basis of the plurality of brightness values comprises determining a quotient of the maximum brightness value and the minimum brightness value.

3. The method according to claim 1,
    wherein the step of determining a plurality of brightness values comprises determining a brightness distribution; and
    wherein the step of determining the waviness index of hair on the basis of the plurality of brightness values comprises determining a value for the breadth of the brightness distribution.

4. The method according to claim 3, further comprising a step of:
    illuminating the recorded hair with diffuse light during the recording of the at least one digital image.

5. The method according to claim 4,
    wherein the step of recording of the at least one digital image comprises the following:
    arranging a camera for recording the digital image in such a way that an angle between a main direction, from which the diffuse light illuminates the hair, and an optical axis of the camera has an angle of at least about 75°.

6. The method according to claim 1, further comprising a step of:
    recording the at least one digital image.

7. The method according to claim 6,
    wherein the step of recording the at least one digital image comprises recording a plurality of digital images, and
    wherein each image of the plurality of digital images shows hair from a different area of a hairstyle.

8. The method according to claim 7,
    wherein the step of determining the waviness index of hair comprises determining a common hairstyle waviness index on the basis of the plurality of brightness values from the plurality of digital images.

9. The method according to claim 1,
    wherein the step of establishing the at least one hair examination region comprises establishing the position and/or shape and/or size of the hair examination region.

10. The method according to claim 1,
    wherein the step of determining and/or establishing of at least one hair examination region comprises:
    determining a hair display region in which the hair is depicted in the digital image; and
    establishing at least part of the hair display region as the at least one hair examination region.

11. The method according to claim 10,
    wherein the at least one hair determination region comprises the entire hair display region.

12. The method according claim 1,
    wherein the digital image is parameterised in a colour space which has a brightness as one parameter.

13. The method according to claim 1, further comprising a step of:
    displaying the determined result on a display device.

14. A device for determining the waviness index of hair, comprising:
    a data processing device; and
    a display device;
    wherein the device is designed to carry out the method according to claim 1.

15. A method for determining an individual hair treatment recommendation, comprising the steps of:
    determining a waviness index of hair according to claim 1; and
    determining and outputting an individual treatment recommendation on the basis of the determined waviness index.

16. The method according to claim 1, wherein:
    the step of determining a plurality of brightness values comprises determining a minimum brightness value and a maximum brightness value; and
    wherein the step of determining the waviness index of hair on the basis of the plurality of brightness values comprises determining a quotient of the maximum brightness value and the minimum brightness value;
    wherein the method further comprises:
    a step of recording a plurality of digital images wherein each image of the plurality of digital images shows hair from a different area of a hairstyle, wherein the step of recording comprises arranging a camera for recording the digital image in such a way that an angle between a main direction, from which the diffuse light illuminates the hair, and an optical axis of the camera has an angle of at least about 75°, wherein the step of determining the waviness index of hair comprises determining a common hairstyle waviness index on the basis of the plurality of brightness values from the plurality of digital images;

step of illuminating the recorded hair with diffuse light during the recording of the at least one digital image; and a step of displaying the determined result on a display device.

17. The method according to claim 16, wherein the digital image is parameterised in a colour space which has a brightness as one parameter.

18. The method according to claim 1, wherein:

the step of determining a plurality of brightness values comprises determining a brightness distribution; and the step of determining the waviness index of hair on the basis of the plurality of brightness values comprises determining a value for the breadth of the brightness distribution;

wherein the method further comprises:

a step of recording a plurality of digital images wherein each image of the plurality of digital images shows hair from a different area of a hairstyle, wherein the step of recording comprises arranging a camera for recording the digital image in such a way that an angle between a main direction, from which the diffuse light illuminates the hair, and an optical axis of the camera has an angle of at least about 75°, wherein the step of determining the waviness index of hair comprises determining a common hairstyle waviness index on the basis of the plurality of brightness values from the plurality of digital images;

step of illuminating the recorded hair with diffuse light during the recording of the at least one digital image; and a step of displaying the determined result on a display device.

19. The method according to claim 18, wherein the digital image is parameterised in a colour space which has a brightness as one parameter.

* * * * *